US00PP28297P2

(12) United States Plant Patent
Heuger

(10) Patent No.: US PP28,297 P2
(45) Date of Patent: Aug. 15, 2017

(54) ***HELLEBORUS* PLANT NAMED 'COSEH 4200'**

(50) Latin Name: *Helleborus×ericsmithii×Helleborus×hybridus*
Varietal Denomination: COSEH 4200

(71) Applicant: Josef Heuger, Glandorf (DE)

(72) Inventor: Josef Heuger, Glandorf (DE)

( * ) Notice: Subject to any disclaimer, the term of this patent is extended or adjusted under 35 U.S.C. 154(b) by 0 days.

(21) Appl. No.: 14/999,210

(22) Filed: Apr. 11, 2016

(51) Int. Cl.
*A01H 5/02* (2006.01)

(52) U.S. Cl.
USPC ..... Plt./439

(58) Field of Classification Search
USPC ..... Plt./439
See application file for complete search history.

*Primary Examiner* — Anne Grunberg
(74) *Attorney, Agent, or Firm* — C. A. Whealy

(57) ABSTRACT

A new and distinct cultivar of *Helleborus* plant named 'COSEH 4200', characterized by its upright and mounding plant habit; uniform and freely flowering habit; dark green-colored leaves; freely and early flowering habit; single pink-colored flowers; and good garden performance.

2 Drawing Sheets

Botanical designation: *Helleborus×ericsmithii×Helleborus×hybridus.*

Cultivar denomination: 'COSEH 4200'.

CROSS-REFERENCED TO CLOSELY-RELATED APPLICATIONS

Title: *Helleborus* Plant Named 'COSEH 4100'
Applicant: Josef Heuger
Filed: Concurrently with this application having application Ser. No. 14/999,209
Title: *Helleborus* Plant Named 'COSEH 4500'
Applicant: Josef Heuger
Filed: Concurrently with this application having application Ser. No. 14/999,211

BACKGROUND OF THE INVENTION

The present invention relates to a new and distinct cultivar of *Helleborus* plant, botanically known as *Helleborus×ericsmithii×helleborus×hybridus* and hereinafter referred to by the name 'COSEH 4200'.

The new *Helleborus* plant is a product of a planned breeding program conducted by the Inventor in Glandorf, Germany. The objective of the breeding program was to create new uniform *Helleborus* plants with unique and attractive plant habit, leaf and flower coloration and resistance to pests common to *Helleborus* plants.

The new *Helleborus* plant originated from a cross-pollination conducted by the Inventor in Glandorf, Germany in February, 2011 of a proprietary selection of *Helleborus×ericsmithii* identified as code number HE 10843, not patented, as the female, or seed, parent with an unnamed seedling selection of *Helleborus×hybridus*, not patented, as the male, or pollen, parent. The new *Helleborus* plant was discovered and selected by the Inventor as a single flowering plant from within the progeny of the stated cross-pollination grown in a controlled greenhouse environment in Glandorf, Germany in November, 2012.

Asexual reproduction of the new *Helleborus* plant by divisions in a controlled environment in Glandorf, Germany since April, 2013 has shown that the unique features of this new *Helleborus* plant are stable and reproduced true to type in successive generations.

SUMMARY OF THE INVENTION

Plants of the new *Helleborus* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'COSEH 4200'. These characteristics in combination distinguish 'COSEH 4200' as a new and distinct *Helleborus* plant:

1. Upright and mounding plant habit.
2. Uniform and freely flowering habit.
3. Dark green-colored leaves.
4. Freely and early flowering habit.
5. Single pink-colored flowers.
6. Good garden performance.

Compared to plants of the female parent selection, plants of the new *Helleborus* and the female parent selection differ primarily in flower color as plants of the female parent selection have creamy white to pink-colored flowers. Compared to plants of the male parent selection, plants of the new *Helleborus* are more uniform and are more freely flowering.

Plants of the new *Helleborus* can be compared to plants of *Helleborus×ericsmithii×Helleborus×hybridus* 'COSEH 4100', disclosed in a U.S. Plant Patent application filed concurrently having application Ser. No. 14/999,209, and *Helleborus×ericsmithii×Helleborus×hybridus* 'COSEH 4500', disclosed in a U.S. Plant Patent application filed concurrently having application Ser. No. 14/999,211. Plants of the new *Helleborus* differ primarily from plants of 'COSEH 4100' and 'COSEH 4500' in flower color as plants of 'COSEH 4100' have red purple to grayed purple-colored flowers and plants of 'COSEH 4500' have white-colored flowers.

Plants of the new *Helleborus* can also be compared to plants of *Helleborus×nigercors* 'COSEH 750', disclosed in U.S. Plant Pat. No. 22,018. In side-by-side comparisons, plants of the new *Helleborus* differ primarily from plants of 'COSEH 750' in flower color as plants of 'COSEH 750' have light green to white-colored flowers.

BRIEF DESCRIPTION OF THE PHOTOGRAPHS

The accompanying colored photographs illustrate the overall appearance of the new *Helleborus* plant showing the colors as true as it is reasonably possible to obtain in colored reproductions of this type. Colors in the photographs may differ slightly from the color values cited in the detailed botanical description which accurately describe the colors of the new *Helleborus* plant.

The photograph on the first sheet is a side perspective view of a typical flowering plant of 'COSEH 4200' grown in a container.

The photograph on the second sheet is a close-up view of a typical flower of 'COSEH 4200'.

DETAILED BOTANICAL DESCRIPTION

The aforementioned photographs and following observations, measurements and values describe plants grown during the autumn and winter in 15-cm containers in a glass-covered greenhouse in Glandorf, Germany and under cultural practices typical of commercial *Helleborus* production. During the production of the plants, day temperatures ranged from 12° C. to 32° C. and night temperatures ranged from 3° C. to 18° C. Plants were 16 months old when the photographs and the description were taken. In the following description, color references are made to The Royal Horticultural Society Colour Chart, 2015 Edition, except where general terms of ordinary dictionary significance are used.

Botanical classification: *Helleborus×ericsmithii×Helleborus×hybridus* 'COSEH 4200'.

Parentage:

- *Female, or seed, parent*.—Proprietary selection of *Helleborus×ericsmithii* identified as code number HE 10843, not patented.
- *Male, or pollen, parent*.—Unnamed seedling selection of *Helleborus×hybridus*, not patented.

Propagation:

- *Type*.—By tissue culture.
- *Time to initiate roots, winter*.—About two months at temperatures about 12° C.
- *Time to produce a rooted young plant, winter*.—About six months at temperatures ranging from 4° C. to 15° C.
- *Root description*.—Thick to thin, fleshy; typically white to brown in color, actual color of the roots is dependent on substrate composition, water quality, fertilizer type and formulation, substrate temperature and physiological age of roots.
- *Rooting habit*.—Sparse.

Plant description:

- *Plant and growth habit*.—Herbaceous perennial; upright and mounding plant habit with flowers held just above and beyond the foliar plane; plant shape, roughly flattened globular; moderately vigorous growth habit; moderate growth rate.
- *Plant height, soil level to top of foliar plane*.—About 24.2 cm.
- *Plant height, soil level to top of flowers*.—About 35.5 cm.
- *Plant diameter* (*area of spread*).—About 50.5 cm.

Leaf description:

- *Arrangement*.—Leaves arranged in a basal rosette; leaves palmately compound with typically five, or occasionally seven, leaflets per leaf.
- *Leaf length*.—About 22.6 cm.
- *Leaf width*.—About 25.3 cm.
- *Leaflet length*.—About 14 cm.
- *Leaflet width*.—About 7.5 cm.
- *Leaf shape*.—Palmate; reniform in outline.
- *Leaflet shape*.—Ovate, elliptic and obovate.
- *Leaflet apex*.—Apiculate.
- *Leaflet base*.—Attenuate.
- *Leaflet margin*.—Serrate; strongly undulate.
- *Leaflet texture and luster, upper surface*.—Smooth, glabrous; slightly rugose; leathery; glossy.
- *Leaflet texture and luster, lower surface*.—Smooth, glabrous; slightly rugose; leathery; moderately glossy.
- *Leaflet venation pattern*.—Pinnate.
- *Leaflet color*.—Developing leaflets, upper surface: Close to 137B. Developing leaflets, lower surface: Close to 148A. Fully developed leaflets, upper surface: Close to darker than between 139A and N189A; venation, close to 143B. Fully developed leaflets, lower surface: Close to 147B; venation, close to between N186C and 200B.
- *Petioles*.—Length: About 14.1 cm. Diameter: About 8 mm. Strength: Strong. Texture and luster, upper and lower surfaces: Smooth, glabrous; moderately glossy. Color, upper and lower surfaces: Close to 144C, heavily speckled and tinged with close to N200B.

Flower description:

- *Flower shape and habit*.—Single rotate flowers arranged solitary or in panicles; freely and uniform flowering habit with about five flowers per inflorescence and about 75 flowers developing per plant; flowers facing outwardly to slightly nodding.
- *Fragrance*.—None detected.
- *Natural flowering season*.—Plants begin flowering about ten months after planting; plants flower during the winter in Germany.
- *Flower longevity on the plant*.—About ten days; flowers not persistent.
- *Flower buds*.—Length: About 2 cm. Diameter: About 1.3 cm. Shape: Ovate. Texture and luster: Glabrous; matte. Color: Close to 145D; towards the apex, close to 182C to 182D; venation, close to 182C to 182D.
- *Inflorescence height*.—About 34.1 cm.
- *Inflorescence diameter*.—About 20.4 cm.
- *Flower diameter*.—About 8.1 cm.
- *Flower depth* (*height*).—About 2.8 cm.
- *Petals*.—Transformed into nectaries.
- *Sepals*.—Quantity and arrangement: About five, arranged in a single whorl. Length: About 4.1 cm. Width: About 3.7 cm. Shape: Broadly ovate. Apex: Obtuse. Base: Cuneate. Margin: Entire; slightly to moderately undulate. Texture and luster, upper and lower surfaces: Glabrous; matte. Color: When opening, upper surface: Close to 157D; towards the apex, slightly tinged with close to 182D. When opening, lower surface: Close to 157D; towards the apex, slightly tinged with close to 182D; venation, close to 182D. Fully opened, upper surface: Close to N155B; toward the margins and apex, tinged with close to 186B to 186D; with development, color becoming closer to N187B and 144A. When opening, lower surface: Close to NN155A; towards the margins and apex, tinged with close to 186B to 186D; with development, color becoming closer to N77C.

*Flower bracts*.—Quantity per flower: Typically one. Length: About 4.1 cm. Width: About 3 cm. Shape: Ovate. Apex: Acute. Base; Broadly cuneate. Margin: Entire; distally, occasionally serrated; slightly undulate. Color, upper surface: Close to 137B. Color, lower surface: Close to 148A; venation, close to between N186C and 200C.

*Peduncles*.—Length: About 27.7 cm. Diameter: About 8 mm. Aspect: About 20° from vertical. Strength: Strong. Texture and luster: Glabrous; moderately glossy. Color: Close to 144C, heavily speckled and flushed with close to 177A.

*Pedicels*.—Length: About 3.9 cm. Diameter: About 2 mm. Aspect: About 20° from peduncle axis. Strength: Moderately strong. Texture and luster: Glabrous; glossy. Color: Close to 177B.

*Reproductive organs*.—Stamens: Quantity per flower: About 90. Filament length: About 1.8 cm. Filament color: Close to NN155C. Anther shape: Reniform; basifixed. Anther size: About 2 mm by 3 mm. Anther color: Close to 150C. Pollen amount: Scarce. Pollen color: Close to 4D. Pistils: Quantity per flower: About five. Pistil length: About 1.5 cm. Stigma diameter: About 0.3 mm. Stigma shape: Club-shaped. Stigma color: Close to 150D. Style length: About 1.475 cm. Style color: Close to 186C to 186D. Ovary color: Close to 150D. Nectaries (transformed petals): Quantity per flower: About 13 to 15. Length: About 1.2 cm. Diameter: About 3 mm. Shape: Tubular, flattened. Texture and luster, inner surface: Smooth, glabrous; matte. Texture and luster, outer surface: Smooth, glabrous; glossy. Color, immature, inner and outer surfaces: Close to 144B to 144C; towards the apex, close to N144B. Color, mature, inner and outer surfaces: Close to 144B to 144C; towards the apex, close to 151B.

*Seeds and fruits*.—Seed and fruit development have not been observed on plants of the new *Helleborus*.

Garden performance: Plants of the new *Helleborus* have been observed to have good garden performance and to tolerate rain, wind and to be suitable for USDA Hardiness Zones 5 through 9.

Pathogen & pest resistance: Plants of the new *Helleborus* have not been observed to be resistant to pathogens and pests common to *Helleborus* plants.

It is claimed:

1. A new and distinct *Helleborus* plant named 'COSEH 4200' as illustrated and described.

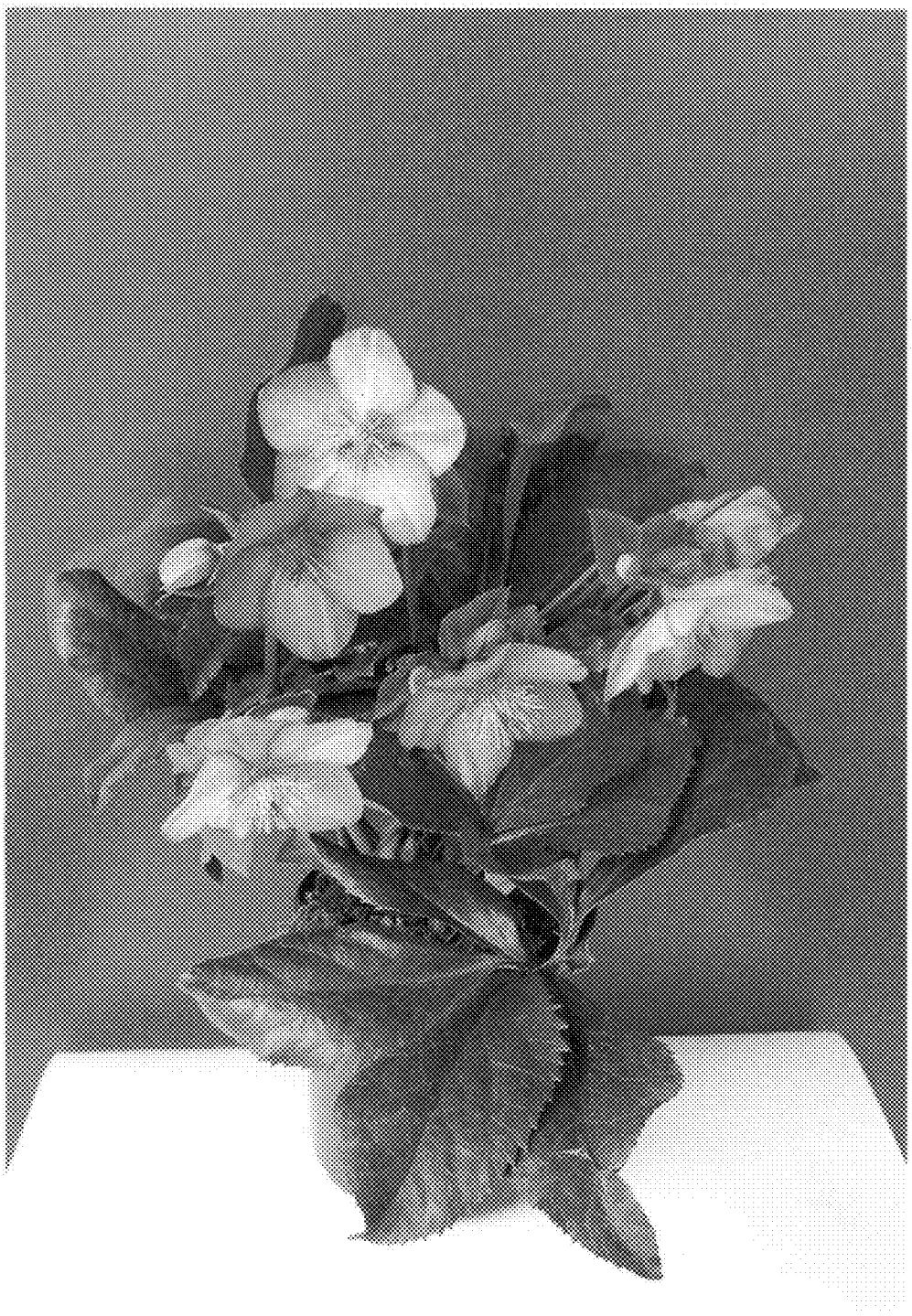

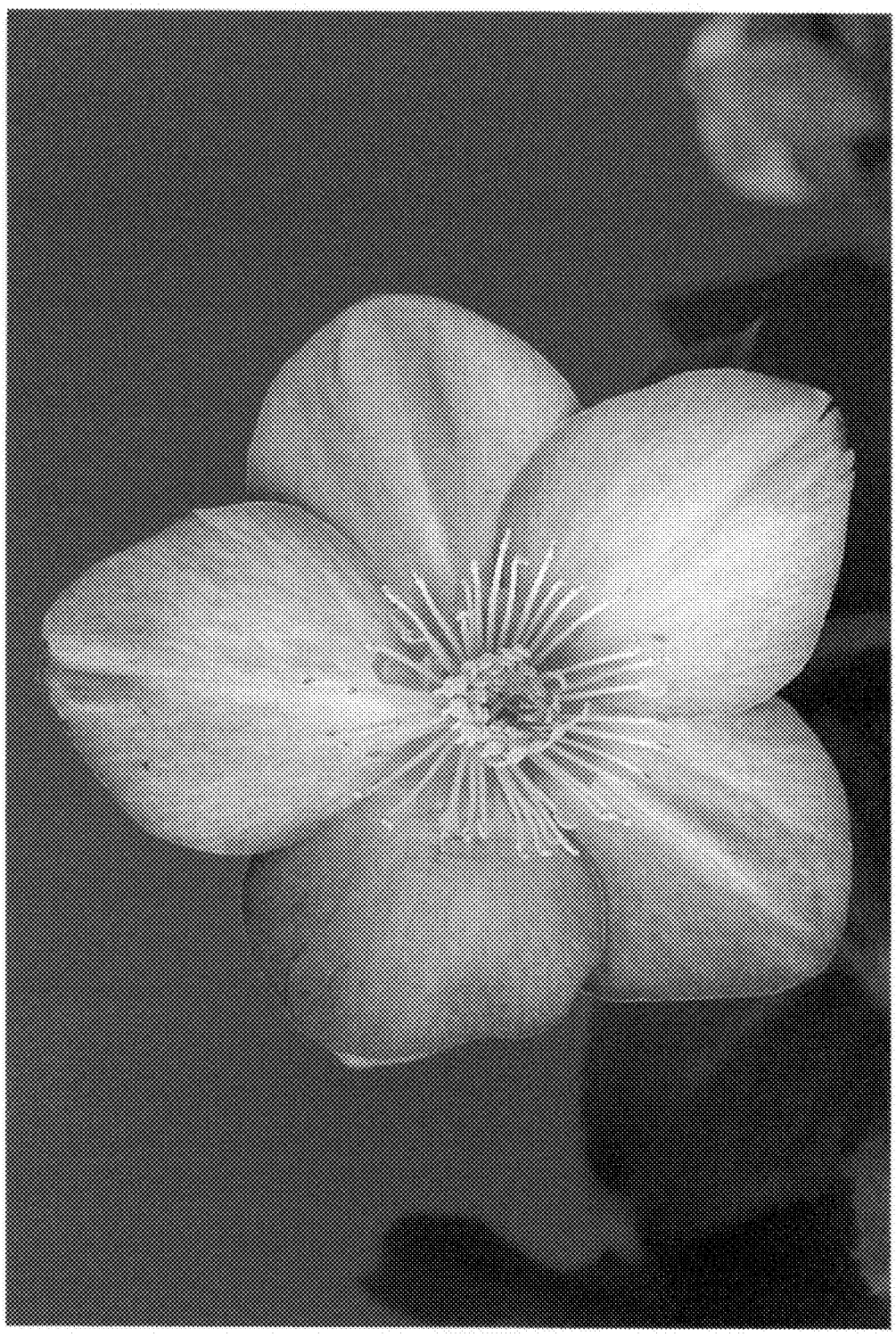

* * * * *